United States Patent [19]

Nishimura et al.

[11] 4,329,025
[45] May 11, 1982

[54] EYE FUNDUS CAMERA HAVING A FLUORESCENT PHOTOGRAPHING DEVICE

[75] Inventors: Shinichi Nishimura; Yoshihiko Hanamura, both of Tokyo, Japan

[73] Assignee: Tokyo Kogaku Kikai Kabushiki Kaisha, Tokyo, Japan

[21] Appl. No.: 117,941

[22] Filed: Feb. 4, 1980

[30] Foreign Application Priority Data

Feb. 9, 1979 [JP] Japan .................. 54/13906

[51] Int. Cl.³ .......................... A61B 3/10; A61B 3/14
[52] U.S. Cl. ......................... 351/7; 351/14; 351/9; 354/62
[58] Field of Search ................ 351/6, 7, 9, 10, 11, 351/14; 354/62

[56] References Cited

U.S. PATENT DOCUMENTS 4,200,376 4/1980 Takeuchi et al. .................. 354/62

Primary Examiner—John K. Corbin
Assistant Examiner—Rodney Bovernick
Attorney, Agent, or Firm—Brumbaugh, Graves, Donohue & Raymond

[57] ABSTRACT

Eye fundus camera having an illumination system provided with a fluorescence exciting filter which can be retractably inserted into the illumination optical path for fluorescent photographing. The intensity of illumination is increased in fluorescent photographing. The data projecting system in the camera includes a data illumination optical path for leading a light from the illumination system and a shutter is provided for at least decreasing the illumination of the data projecting system in fluorescent photographing.

7 Claims, 8 Drawing Figures

EYE FUNDUS CAMERA HAVING A FLUORESCENT PHOTOGRAPHING DEVICE

The present invention relates to eye fundus cameras equipped with fluorescent photographing devices and, more particularly to data taking devices for such eye fundus cameras.

In eye fundus cameras, it is preferable to provide a fluorescent photographing arrangement with which strong illuminations are applied to the eye of a patient who has previously been injected with a fluorescent agent so that fluorescent light is generated and photographs are taken as the agent passes through the blood vessels in the eye fundus to thereby make it possible to analyze in time basis the blood flow in the eye fundus. For the purpose, the illumination system of the eye fundus camera is provided with a fluorescence exciting filter which can be retractably inserted into the illuminating path so that the illumination light is passed through the filter when it is inserted into the illuminating path whereby a fluorescence exciting light is projected to the patient's eye. Further, in order to obtain photographs of high contrast, it is also desirable to provide the photographing optical system with a fluorescent filter which blocks the fluorescence exciting light but allows the fluorescent light to pass therethrough.

In fluorescent photographing, the film as used has a speed which is approximately four times as fast as that of a conventional color picture film and the intensity of the illuminating light must be approximately six times as large as that in a conventional color photographing. It should therefore be noted that problems are encountered in illuminating the data taking device. In general, eye fundus cameras are required to have data taking devices both for conventional color photographings and for fluorescent photographings. In a conventional color photographing, it is necessary for the purpose of film indexing to designate the data for each patient and, in a fluorescent photographing, it is further required in addition to the above data taking to designate the time as counted from the instance of injection of the fluorescent agent. In designing such data taking system, it is preferable from the view points of manufacturing cost and convenience of operation to utilize the light from the illumination system for illuminating the data indicating panel rather than to provide a separate light source for the specific purpose. However, in the aforementioned type of eye fundus camera provided with a fluorescent photographing device, where the illumination of the data indicating panel is properly determined for a conventional photographing, an excessively strong illumination will be applied in fluorescent photographing since the intensity of the light source in the illumination system will be increased at that time.

It is therefore an object of the present invention to provide an eye fundus camera having a fluorescent photographing device in which illumination in the data taking system can be decreased in the fluorescent photographing than in the normal photographing.

Another object of the present invention is to provide an eye fundus camera having a fluorescent photographing device and a data taking system which utilizes the light from the illumination system and is provided with means for restricting the illumination light to the data taking system in fluorescent photographing so that an excessive illumination can be avoided.

According to the present invention, the above and other objects can be accomplished by an eye fundus camera comprising objective lens means adapted to be placed opposed to a patient's eye, an illumination system including an illumination path for projecting an illumination light to the patient's eye through the objective lens means, an observing and photographing optical system including an imaging optical path for focusing the light as reflected at fundus of the patient's eye to produce an image of the eye fundus on an image plane, fluorescence exciting filter means provided in the illumination system so that it can be retractably inserted into the illumination path, fluorescence filter means provided in said photographing optical system so that it can be retractably inserted into the imaging optical path, means for increasing intensity of the illumination light when the fluorescence exciting filter means is inserted into the illumination path, data indicating means, data illuminating optical path for leading a portion of the light in the illumination system to the data indicating means, a data projecting optical system for directing the light as reflected at the data indicating means to the image plane in the photographing optical system, means for restricting at least a portion of the light to said data indicating means when at least one of the fluorescence exciting filter means and the fluorescent filter means is inserted into the illumination path.

It will be noted that the novel features of the present invention are in that the data illuminating optical path is provided for leading a portion of the light in the illuminating system to the data indicating and that the means is provided for restricting at least a portion of the light to the data indicating means when the fluorescence exciting filter means is inserted into the illumination path. When the data indicating means is positioned in a place where free light from the illumination system reaches, the data illuminating optical path may be totally blocked by the restricting means when the fluorescence exciting filter is inserted into the illumination path so that the illumination of the data indicating means may be made only by the free light from the illuminating system. For example, the data illuminating optical path may be comprised of an optical guide having one end adjacent to the fluorescence exciting filter means so that the end is covered by a shutter provided on the filter means when the filter means is inserted into the illumination path. Alternatively, the shutter may be provided on the fluorescent filter in the photographing system so that it blocks the data illumination light when the fluorescent filter is in the imaging optical system.

The above and other objects and features of the present invention will become apparent from the following descriptions of a preferred embodiment taking reference to the accompanying drawings, in which.

Figure 1:
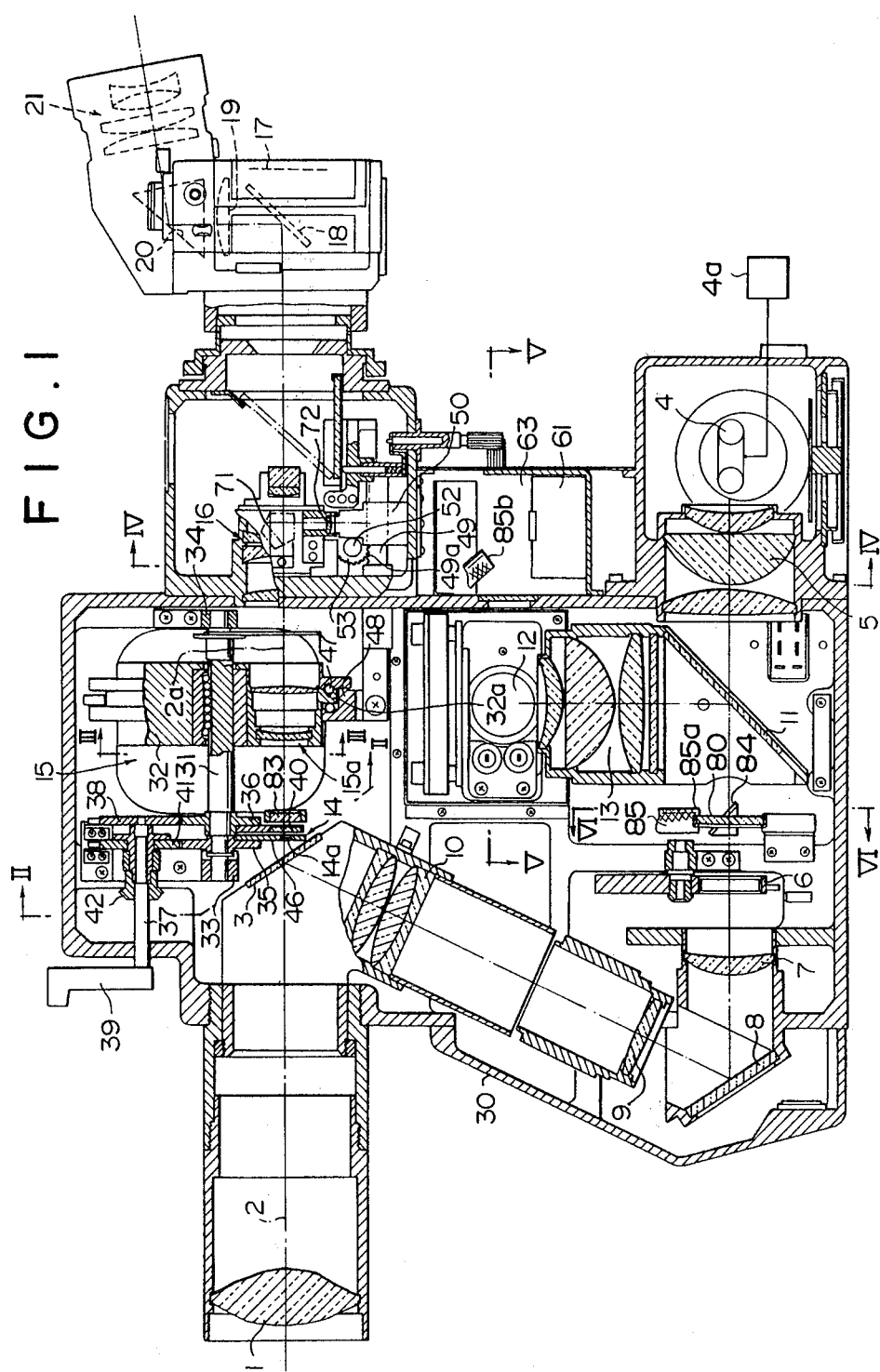
FIG. 1 is a sectional view of an eye fundus camera embodying the features of the present invention.

Referring now to the drawings, particularly to FIG. 1, there is shown an eye fundus camera including a housing 30 provided with a non-spherical objective lens 1 which is adapted to be placed against a patient's eye. The objective lens 1 has an optical axis 2 on which an apertured mirror 3 is obliquely arranged substantially in conjugate with the pupil of the patient's eye with respect to the objective lens 1. The eye fundus camera has an illumination system including a photographing xenon lamp 4. The light from the lamp 4 is passed through a condenser lens 5, a ring-shaped aperture 6 and a lens 7 to a mirror 8 to be reflected thereby. The light reflected by the mirror 8 is then passed through lenses 9 and 10 to the apertured mirror 3 to be reflected thereby toward the objective lens 1. Thus, the illumination light is passed through the objective lens 1 and the pupil of the patient's eye to be projected to the eye fundus. Between the condenser lens 5 and the ring-shaped aperture 6, there is disposed a half-transparent mirror 11, and a tungusten lamp 12 is provided so that the light from the lamp 12 is passed through a condenser lens 13 to the mirror 11 to be reflected thereby toward the ring-shaped aperture 6.

The eye fundus camera further has an observing and photographing optical system including an aperture 14 which is located behind the apertured mirror 3 substantially in conjugate with the pupil of the patient's eye with respect to the objective lens 1. The photographing optical system has an optical axis 2a along which a power changing and focusing lens system 15 and an imaging lens system 16 are arranged. Thus, the light reflected at the eye fundus is passed through the aperture in the mirror 3 and then through the aperture 14 and the lens systems 15 and 16 to be focused on a photographing film plane 17.

In the illustrated embodiment, the lens system 15 is designed for performing power changing and focusing and comprised of a plurality of power changing lenses 15a, 15b and 15c which have different powers of magnification and are adapted to be alternately inserted into the photographing optical path. The lenses are also arranged for movement along the optical axis 2a for focusing.

In front of the film plane 17, there is disposed a retractable mirror 18 so that the light from the imaging lens system 16 is reflected upwardly by the mirror 18 when the mirror 18 is in the position shown in FIG. 1. The light reflected by the mirror 18 is focused on an image plane 19 and the image on the plane 19 can be observed through a mirror 20 and an eye lens 21. The retractable mirror 18 may be substituted by a half-transparent mirror or prism.

The lens system 15 includes a rotatable member 32 mounted on a rotatable shaft 31 in such a manner that it rotates with the shaft 31 but is axially movable with respect to the shaft 31. The aforementioned lenses 15a, 15b, and 15c are mounted on the rotatable member 32. The rotatable shaft 31 is supported at the opposite ends for rotation by a pair of bearings 33 and 34 and has a gear 35 secured thereto adjacent to one end thereof. On the shaft 31, there is further mounted a gear 36 which is rotatable with respect to the shaft 31 and located adjacent to the gear 35. The gear 36 is in meshing engagement with a gear 38 which is fixed to an actuating shaft 37 so that the gear 36 can be rotated through the shaft 37. For the purpose, the shaft 37 is provided with a lever 39. The gear 36 has refractive power correcting lenses 40 so that an appropriate one of the lenses 40 is placed in the photographing optical path in accordance with the refractive power of the patient's eye.

Figure 2:
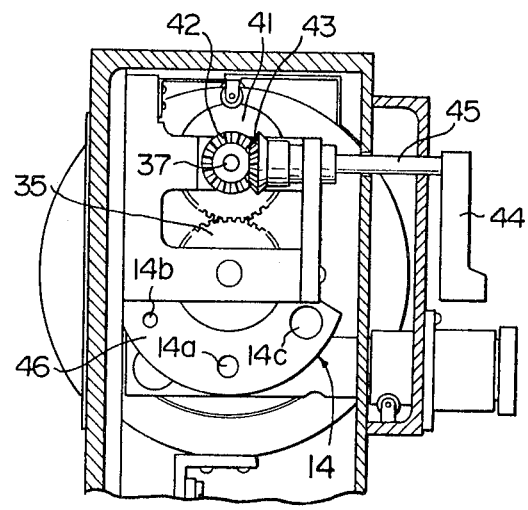
FIG. 2 is a sectional view taken along the line II—II in FIG. 1.
Figure 3:
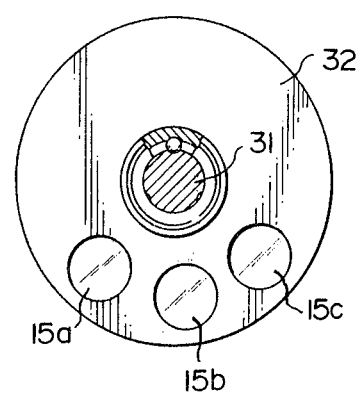
FIG. 3 is a view as seen along the line III—III and in the direction of arrows in FIG. 1.

The gear 35 secured to the rotatable shaft 31 is in meshing engagement with a gear 41 which is rotatably mounted on the actuating shaft 37. The gear 41 has a bevel gear 42 which is secured thereto and in turn in engagement with a bevel gear 43 as shown in FIG. 2. The bevel gear 43 is secured to a power changing shaft 45 which has a handle 44. It should therefore be understood that the rotatable shaft 31 and the member 32 are rotated by the handle 44 to locate an appropriate one of the lenses 15a, 15b and 15c in the photographing optical path.

The gear 35 has an aperture plate 46 which is secured thereto and constitutes the aforementioned aperture mechanism 14. The aperture plate 46 is formed with a plurality of apertures 14a, 14b and 14c of different diameters as shown in FIG. 2 and an appropriate one of the apertures is located in the photographing optical path in accordance with the magnification power of the power changing lens system 15. According to the arrangement, an appropriate aperture diameter can automatically be determined in accordance with the magnification power of the photographing optical system so that it is possible to maintain a substantially constant brightness and to exclude harmful light other than the imaging light bundle to thereby obtain images of high quality.

The rotatable member 32 has a peripheral flange 32a with which a focusing ring 48 is engaged through a ball bearing 47. The ring 48 is secured to a rack member 49 which has a rack 49a and is carried by a guide member 50 for axial movement. The rack 49a on the member 49 is engaged with a pinion 53 provided on a focusing shaft 52 which is adapted to be rotated by a focusing knob 51. It should therefore be understood that, for focusing, the rack member 49 is axially moved by rotating the focusing knob 51 to thereby move the rotatable member 32 through the ring 48 axially along the shaft 31.

Figure 5:
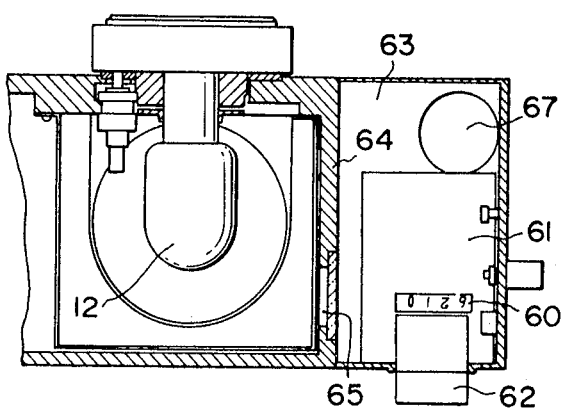
FIG. 5 is a sectional view taken along the line V—V in FIG. 1.
Figure 4:
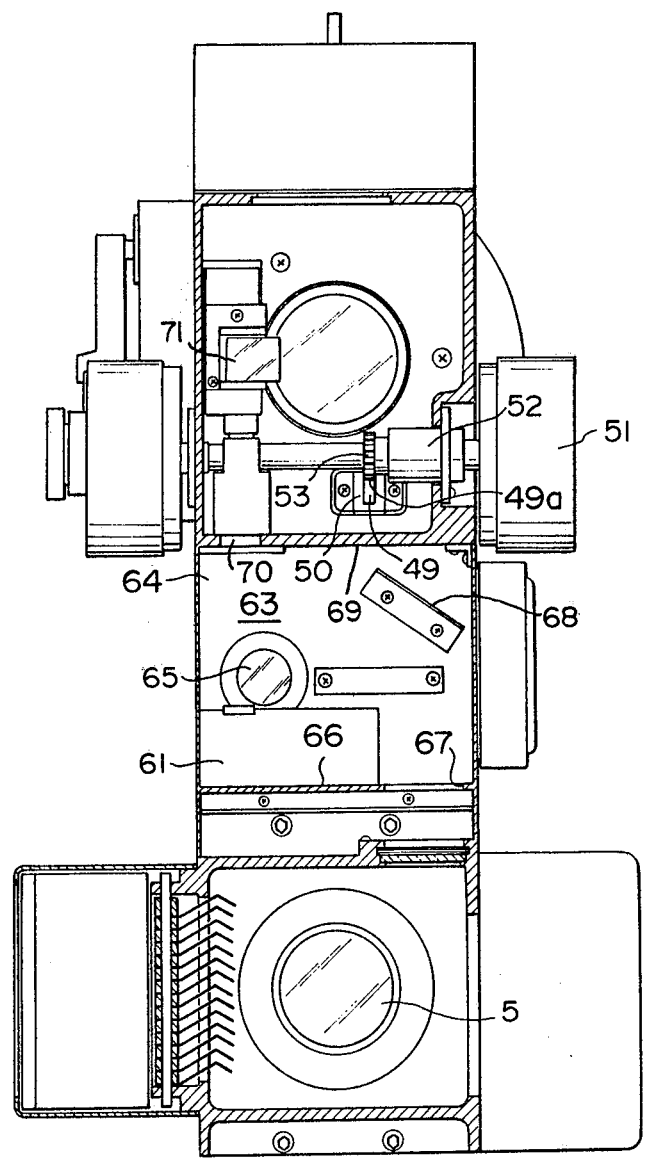
FIG. 4 is a sectional view taken along the line IV—IV in FIG. 1.

The eye fundus camera further includes a data projecting system which includes, as shown in FIG. 5, a counter 61 having an indicating panel 60 and a data card 62 adapted to be placed on the counter 61 adjacent to the indicating panel 60. As shown in FIGS. 1, 4 and 5, the counter 61 is located in a chamber 63 which is defined above the lamp 4 and behind the lamp 12. The chamber 62 is separated from the lamp 4 by a wall 64 which has an opening 65 so that free light from the lamp 12 is passed through the opening 65 to the chamber 63 to illuminate the indicating panel 60 of the counter 61 and the data card 62.

The chamber 63 is further separated from the lamp 12 by a wall 6 which has an opening 67 so that free light from the lamp 12 is passed through the opening 67 to the chamber 63. In the chamber 63, there is provided a mirror 68 for reflecting the light from the opening 67 to the indicating panel 60 of the counter 61 and the data card 62.

The chamber 63 has an upper wall 69 which is formed with an opening 70 at a position directly above the indicating panel 60 and the data card 62 so that the light reflected at the indicating panel 60 and the data card 62 is led through the opening 70 to one side of the photographing optical axis. On the side of the photographing optical axis, there is provided a pentagonal prism 71 which serves to reflect the light from the opening 70 rearwardly to the film 17. A focusing lens 72 is provided for producing images of the counter indicating panel 60 and the data card 62.

Figure 6:
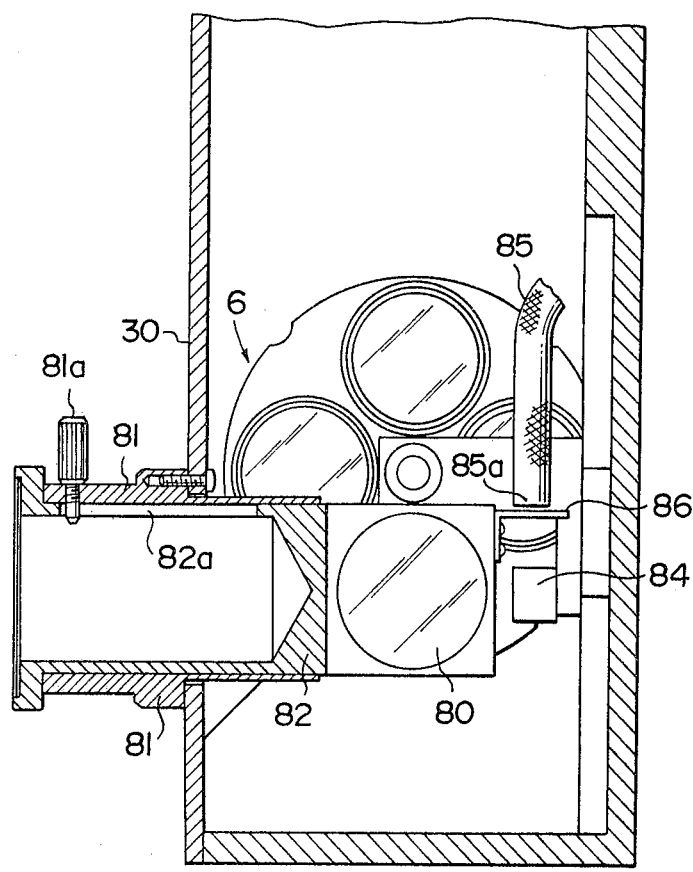
FIG. 6 is a sectional view taken along the line VI—VI in FIG. 1.

Referring to FIG. 1, it will be noted that the illumination system includes a fluorescence exciting filter 80 which is retractably inserted into the illumination optical path between the half-transparent mirror 11 and the ring-shaped aperture 6. As shown in FIG. 6, the filter 80 is carried by a filter support 82 which is slidable along a guide member 81 provided on the housing 30. The filter support 82 is formed at the upper edge with a slot 82a which is engaged with a guide pin 81a on the guide member 81 so that the filter support 82 is movable between an insert position wherein the center of the filter 80 is aligned with the illumination optical axis and a retracted position wherein the filter 80 is retracted from the illumination path. In the photographing optical system, there is provided a fluorescent filter 83 which can be retractably inserted into the photographing optical path between the lens system 15 and the lens 40.

As shown in FIGS. 1 and 6, the illumination system is provided at one side of the illumination optical path with a mirror 84 which reflects a portion of the illumination light upwardly. An optical guide 85 is provided with its one end 85a in the path of the light reflected by the mirror 84. The other end 85b of the optical guide 85 is located in the chamber 63 so that the light therefrom is directed to the counter 61 and the data card 62. The filter support 82 has a shutter plate 86 mounted on the inner end thereof so that the shutter plate 86 covers the end 85a of the optical guide 85, when the filter 80 is inserted into the illumination path, so as to block the illumination light to the optical guide 85. When the filter 80 is in the retracted position, a portion of the illumination light is directed through the optical guide 85 to illuminate the counter 61 and the data card 62 together with the free light from the opening 65 and 67.

The photographing illumination lamp 4 is associated with an intensity controller 4a which functions to increase the intensity of the lamp 4 when the filter 80 is inserted into the illumination path. In this instance, however, the illumination light to the optical guide 85 is blocked by the shutter plate 85 so that the counter 61 and the data card 62 are illuminated only by the free light through the openings 65 and 67. It is therefore possible to avoid excessive exposure. One of the openings 65 and 67 may be omitted so that the illumination in photographing may be performed only by the free light through only one of the openings 65 and 67.

Figure 7:
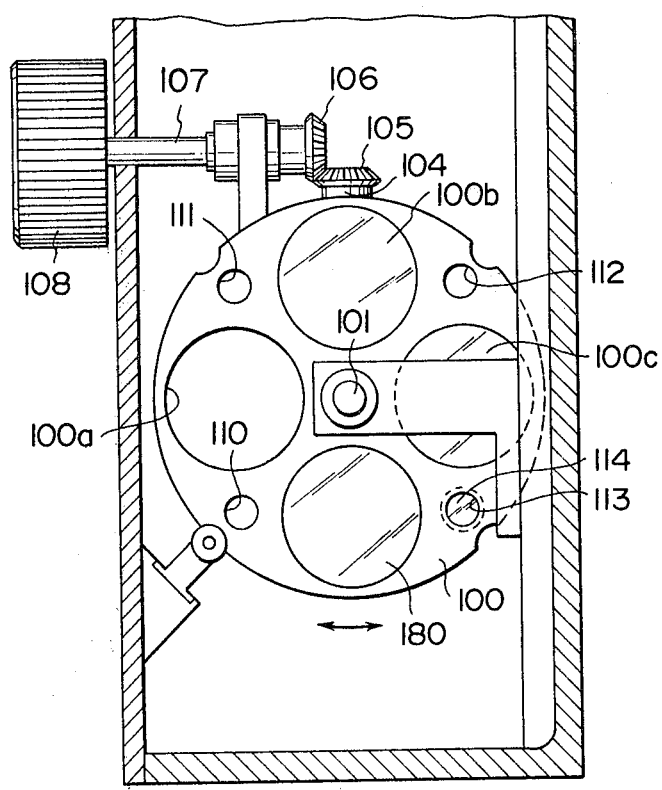
FIG. 7 is a sectional view corresponding to FIG. 6 but showing another embodiment of the present invention; and, FIG. 8 is a side view of the structure shown in FIG. 7.
Figure 8:
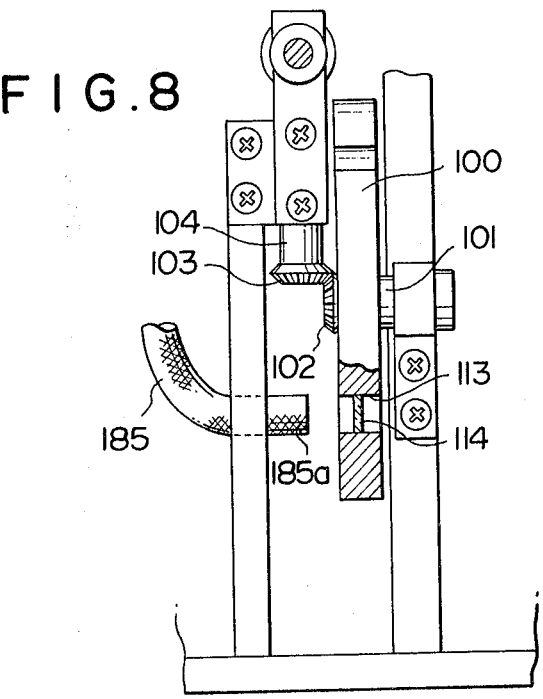

Referring now to FIGS. 7 and 8 which show another embodiment of the present invention, the eye fundus camera includes a rotatable disc 100 which is mounted on a rotatable shaft 101 and carries a fluorescence exciting filter 180. The rotatable shaft 101 has a bevel gear 102 which is in meshing engagement with a bevel gear 103 on a counter-shaft 104 having a second bevel gear 105 which is in meshing engagement with a bevel gear 106 on a shaft 107. The shaft 107 is provided with a knob 108 so that the rotatable disc 100 can be rotated by actuating the knob 108 through the aforementioned gear train.

The rotatable disc 100 is formed with an opening 100a and further filters 100b and 100c which may optionally be inserted into the illumination path. An optical guide 185 which is similar in function to the optical guide 85 in the previous embodiment has an end 185a positioned against the disc 100 and the disc 100 is formed with apertures 110, 111 and 112 so that one of them is aligned with the end 185a of the optical guide 185 when one of the opening 100a and the filters 100b and 100c is placed in the illumination path. When the fluorescence exciting filter is inserted into the illumination path, the end 185a of the optical guide 185 is aligned with a further aperture 113 in the disc 100 which is provided with an ND filter 114 so that the light into the optical guide 185 is decreased. In the apertures 111 and 112, there may be provided further ND filters which may respectively correspond to the filters 100b and 100c.

The invention has thus been shown and described with reference to specific embodiments, however, it should be noted that the invention is in no way limited to the details of the illustrated structures but changes and modifications may be made without departing from the scope of the appended claims. For example, the shutter or data illumination light restricting ND filter may be moved to its operative position in response to the movement of the fluorescent filter into the photographing optical path. Further, such shutter or the data illumination light restricting ND filter may not necessarily cover the whole area of the data illumination path but may only partially cover the path.

We claim:

1. Eye fundus camera comprising objective lens means adapted to be placed so that it is opposed to a patient's eye, an illumination system including an illumination path for projecting an illumination light to the patient's eye through the objective lens means, an observing and photographing optical system including an imaging optical path for focusing the light as reflected at fundus of the patient's eye to produce an image of the eye fundus on an image plane, fluorescence exciting filter means provided in the illumination system so that it can be retractably inserted into the illumination path, fluorescence filter means provided in said photographing optical system so that it can be retractably inserted into the imaging optical path, means for increasing intensity of the illumination light when the fluorescence exciting filter means is inserted into the illumination path, data indicating means, data illuminating optical path for leading a portion of the light in the illumination system to the data indicating means, a data projecting optical system for directing the light as reflected at the data indicating means to the image plane in the photographing optical system, means for restricting at least a portion of the light to said data indicating means when at least one of the fluorescence exciting filter means and the fluorescent filter means is inserted into the illumination path.

2. Eye fundus camera in accordance with claim 1 in which means is provided for leading free light from the illumination system to the data indicating means, said restricting means including shutter means for completely blocking the data illuminating optical path.

3. Eye fundus camera in accordance with claim 1 in which said restricting means includes light reducting filter means which is adapted to cover the data illuminating optical path.

4. Eye fundus camera in accordance with claim 1 in which said data illuminating optical path is arranged to pass by the fluorescence exciting filter means, said fluorescence exciting filter means carrying said restricting means so that the data illuminating optical path is blocked by the restricting means when the fluorescence exciting filter means is inserted into the illumination path.

5. Eye fundus camera in accordance with claim 1 in which said data illumination optical path is comprised of an optical guide having one end located adjacent to the fluorescence exciting filter means and the other end against said data indicating means, said fluorescence exciting filter means carrying said restricting means so that said one end of the optical guide is covered by said restricting means when the fluorescence exciting filter means is inserted into the illumination optical path.

6. Eye fundus camera in accordance with claim 5 in which said restricting means is a shutter.

7. Eye fundus camera in accordance with claim 5 in which said restricting means is a light reducing filter.

* * * * *